US008514488B2

(12) United States Patent
Lücke et al.

(10) Patent No.: US 8,514,488 B2
(45) Date of Patent: Aug. 20, 2013

(54) TUBE FOR A SURGICAL MICROSCOPE

(75) Inventors: Christian Lücke, Oberkochen (DE); Hartmut Gärtner, Oberkochen (DE); André Müller, Königsbronn-Zang (DE); Martin Schneider, Königsbronn (DE); Alfons Abele, Schwäbisch Gmünd (DE); Nadine Kolster, Oberkochen (DE); Dirk Holzmann, Pforzheim (DE); Wolfgang Robra, Bad Wildbad (DE); Bernd Rudisile, Keltern (DE); Michael Czerwinski, Pforzheim (DE)

(73) Assignee: Carl Zeiss Meditec AG, Jena (DE)

( * ) Notice: Subject to any disclaimer, the term of this patent is extended or adjusted under 35 U.S.C. 154(b) by 346 days.

(21) Appl. No.: 12/805,663

(22) Filed: Aug. 12, 2010

(65) Prior Publication Data

US 2011/0043904 A1 Feb. 24, 2011

(30) Foreign Application Priority Data

Aug. 19, 2009 (DE) .......................... 10 2009 037 921

(51) Int. Cl.
*G02B 21/00* (2006.01)
*A61B 19/00* (2006.01)
*G02B 21/24* (2006.01)

(52) U.S. Cl.
CPC ............ *A61B 19/5223* (2013.01); *G02B 21/24* (2013.01)
USPC .......................................... 359/384; 359/368

(58) Field of Classification Search
USPC ................................................. 359/368–384
See application file for complete search history.

(56) References Cited

U.S. PATENT DOCUMENTS

| 2,439,526 | A | * | 4/1948 | Ott ................................. 359/384 |
| 4,175,826 | A | * | 11/1979 | Blaha et al. .................... 359/377 |
| 4,576,450 | A | * | 3/1986 | Westphal ....................... 359/384 |
| 5,543,962 | A | * | 8/1996 | Kitajima et al. ............... 359/384 |
| 6,188,515 | B1 | * | 2/2001 | Nihoshi ......................... 359/384 |
| 6,204,963 | B1 | * | 3/2001 | Grafenhain et al. .......... 359/384 |
| 7,158,293 | B2 | * | 1/2007 | Hund et al. .................... 359/384 |
| 7,256,934 | B2 | | 8/2007 | Bihr et al. |
| 7,265,899 | B2 | * | 9/2007 | Morita .......................... 359/384 |
| 7,583,435 | B2 | * | 9/2009 | Euteneuer et al. ............. 359/384 |
| 2009/0244704 | A1 | * | 10/2009 | Kolster et al. ................. 359/506 |

FOREIGN PATENT DOCUMENTS

DE 297 07 144 U 8/1998

* cited by examiner

*Primary Examiner* — Thong Nguyen
(74) *Attorney, Agent, or Firm* — Walter Ottesen P.A.

(57) ABSTRACT

A tube of a surgical microscope has a base part, intermediate part pivotable about a rotational axis on the base part, and an ocular part pivotable about a rotational axis on the intermediate part. The imaging beam path is guided through the base part, intermediate part and pivotable ocular part. The tube has a tube lens system which transfers a parallel imaging beam path into an intermediate image. The parallel imaging beam path enters via an opening in a connecting piece of the base part. The tube has a first displaceable mirror element movable about the rotational axis on the base part. The tube has a further displaceable mirror element movable on the intermediate part about the rotational axis. The first mirror element directs the imaging beam path to the further mirror element. The first mirror element and further mirror element are mounted in the imaging beam path between a lens unit having positive refractive power and a lens unit having negative refractive power.

13 Claims, 10 Drawing Sheets

TUBE FOR A SURGICAL MICROSCOPE

CROSS REFERENCE TO RELATED APPLICATION

This application claims priority of German patent application no. 10 2009 037 921.5, filed Aug. 19, 2009, the entire content of which is incorporated herein by reference.

FIELD OF THE INVENTION

The invention relates to a tube for a surgical microscope, having an imaging beam path guided via a base part, via an intermediate part pivotable about a rotational axis on the base part and via an ocular part pivotable about a rotational axis on the intermediate part. The tube further includes a tube lens system which passes a parallel imaging beam path, which enters via an opening in a connecting piece of the base part, into an intermediate image. The tube further includes a first adjustable mirror element which can be moved about the rotational axis on the base part and a further adjustable mirror element which can be moved about the rotational axis on the intermediate part. The first mirror element directs the imaging beam path, which enters via the connecting piece, to the further mirror element.

BACKGROUND OF THE INVENTION

A tube of the above kind is known from DE 297 07 144 U1. There, a binocular tube for a surgical microscope is described. The tube has three housing parts through which the imaging beam path is guided and these housing parts are connected to each other by two rotational joints in a pivotably movable manner. The tube contains a first adjustable mirror element and a second adjustable mirror element. The mirror elements are mounted in the rotational axes of the rotational joints and direct the imaging beam path to the oculars of the tube. The imaging beam path enters via a tube lens having positive refractive power.

SUMMARY OF THE INVENTION

It is an object of the invention to provide a tube for a surgical microscope having very good ergonomic characteristics and a very good imaging quality.

This object is achieved by a tube of the kind mentioned above which contains a tube lens system configured as a telesystem. The tube lens system has a lens unit having positive refractive power and a lens unit having negative refractive power. The first mirror element and the second mirror element are disposed in the imaging beam path between the lens unit having positive refractive power and the lens unit having negative refractive power.

A telesystem includes a lens unit having positive refractive power and contains a lens unit whose refractive power is negative.

The invention is based on the idea that the optical path length in the tube lens system can be significantly shortened by means of a telesystem in order to provide structural space for additional optical components in a tube. Furthermore, the image field curvature of the intermediate image in the tube can be reduced or prevented by means of a telesystem.

DETAILED DESCRIPTION OF THE INVENTION

In order to ensure the compatibility of component groups of a surgical microscope, manufacturers of surgical microscopes establish the following standard measurements for: the size of the intermediate image in the binocular tube, the focal length of the tube lens system, and the exit pupil. For a predetermined focal length of the tube lens system, when a telesystem is used as a tube lens system, the optical path length of the imaging beam path between the lens unit having positive refractive power and the intermediate image in the tube is less than for a tube having a tube lens system that only has a lens unit having positive refractive power.

A tube for a surgical microscope is designed for the connection to a base body of the surgical microscope wherein the microscope main objective is mounted and which contains a magnification system.

The position of the exit pupil of a tube having a tube lens system formed as a telesystem is primarily determined by the distance of the lens unit of positive refractive power of the telesystem from the exit pupil of the magnification system in the surgical microscope base body and the refractive power of the lens unit having negative refractive power of the telesystem.

An ergonomically favorably configured tube enables a viewing person especially to move the ocular in-view toward and far away from the surgical microscope base body. A further adjusting region of the tube requires a comparatively long optical path length from the opening on the connecting piece of the base part up to the intermediate image which can be viewed by a viewing person through an ocular having magnification.

In a tube having good ergonomic characteristics and which is movable about two rotational axes and has a base part, an intermediate part, and an ocular part, the mechanical distance of the opening in the base part of the tube and a movable mirror element, which is mounted on the first rotational axis, need be about as large as the distance between the first and second mirror elements in the tube, which is disposed at the second rotational axis. A further adjusting range is then covered by pivoting of the ocular part and the base part about the rotational axis of the tube.

In the tube of the invention, the mirror elements, which deflect the imaging beam path, are mounted between the lens unit of positive refractive power and a lens unit of negative refractive power of a telesystem. For this reason, it can be achieved that the ratio of the optical path length between the mirror elements in the intermediate part of the tube and the optical path length from the opening in the connecting piece of the tube to the first mirror element can be ⅔ or even more. The optical path length from the opening in the connecting part of the tube up to the position of the intermediate image is the same as for a tube having a tube lens whose focal length corresponds to the refractive power of the telesystem and which is mounted in the entry opening of the tube. The optical path length between the opening in the connecting part of the tube up to the position of the intermediate image can then amount to approximately 3½ times the optical path length from the entry opening of the tube up to the first mirror element.

In particular, the invention is based on the idea that by arranging the lens unit having positive refractive power at a distance from the entry opening of the tube, in whose base part a structural space is provided which is available especially for a beam splitter or an afocal system, for example, a magnification system in the form of a Galilei system or zoom system.

A realization of the invention is especially that very good imaging qualities in a tube are combined with excellent ergonomic qualities because of the arrangement of two mirror elements in a tube between the lens unit having positive refractive power and the lens unit having negative refractive power of a telesystem whose focal length lies in the range between 165 mm and 220 mm with each of these mirror elements being pivotable about a rotational axis running perpendicular to the optical axis of the imaging beam path.

Large structural space for a magnification system, which is arranged in the tube, or for a beam splitter arrangement for the in-coupling or out-coupling of an imaging beam path is provided in that the optical path length between the lens unit having positive refractive power and the first adjustable mirror element is held less than the optical path length between the opening in the connecting piece and the lens unit having positive refractive power.

Preferably, the tube lens system is configured for a stereoscopic object viewing. The tube lens system then has a left and right tube system which is passed through by a left and right stereoscopic imaging beam path. The base part and the intermediate part of the tube can be configured to be very narrow and space-saving in that the stereoscopic imaging beam path having constant stereo basis is guided from the opening in the connecting piece to the second mirror element.

The invention is also based on the idea that the tube can be folded together in a small space when the base part has a base part housing and the intermediate part has an intermediate part housing, in which connection the intermediate part on the base part is movable between a folded position and an unfolded position and the base part housing has a housing section whose outer contour is configured with a geometry accommodating the outer contour of the intermediate part housing in the folded position. Then, the intermediate part housing can be pivoted tightly against the base part housing.

The invention is also based on the idea of guiding, in a tube, the imaging beam path through an ocular part which is supported on the intermediate part in a pivotably movable manner and which has an ocular part housing. The ocular part can be moved against the intermediate part between a folded position and an unfolded position. The ocular part housing has a housing section whose outer contour is configured with a geometry accommodating the outer contour of the intermediate part housing when in the folded position. These measures ensure that the ocular part can be applied on the intermediate part in a very tight and space-saving manner.

A further idea of the invention is that, for the movement of the tube, large pivot angles can be obtained in the pivot axes, without a vignetting of the imaging beam path, which passes through the tube, taking place in that a housing covering is provided which is movable relative to the base part and/or the ocular part for covering the imaging beam path passing through the base part. The invention also lies in that a housing covering, which is movable relative to the ocular part, is provided for covering the imaging beam path passing through the ocular part.

For this purpose, it is advantageous to configure the housing covering with a flexible cover section and a rigid cover section. The flexible cover section and the rigid cover section are connected via a hinge. This hinge can be configured as a film hinge. The housing cover itself is advantageously made of plastic and can be manufactured, for example, as an injection molded part. Basically, it is, however, also possible to provide a lamella mechanism for the housing cover.

Pivoting the intermediate part about the rotational axis on the base part, the rigid cover section carries out a rotational movement about the rotational axis on the base part. Correspondingly, the rigid cover section rotates with a pivoting of the ocular part about the rotational axis on the intermediate part when the ocular part is moved about the rotational axis on the intermediate part. The flexible cover section is guided into a slit-shaped receptacle on the base part or on the ocular part. The slit-shaped receptacle acts as a coulisse-type guide.

The housing cover is fixed in the intermediate part. Advantageously, two identically configured housing covers, which are connected to each other, are provided for covering the imaging beam path passing through the base part and for covering the imaging beam path passing through the ocular part.

The lens unit having a negative refractive power is arranged in the ocular part. The ocular part includes a section hinged to the intermediate part and a further section having a receptacle for an ocular. This further section is accommodated on a rotational joint so as to be pivotable about the optical axis of the imaging beam path. A Porro prism for image reversal is disposed in the further section. A drive is provided for pivoting the further section. This enables an adjustment of the pupil distance of the ocular of the tube. The lens system having negative refractive power is arranged between the second mirror element and the Porro system for image reversal.

It is advantageous to position an afocal magnification system between the lens system having positive refractive power and the opening in the connecting piece. The afocal magnification system can be configured as a Galilei changer. When the first lens of the afocal magnification system refracts the parallel imaging beam path toward the optical axis, the afocal magnification system operates to oppose a darkening of the edge regions of the intermediate image in the tube or a vignetting of the intermediate image. Furthermore, an adjustable magnification system in the tube facilitates a variation of the magnification of the surgical microscope with this magnification being adjustable by means of a magnification system in the surgical microscope base body.

To counter the above-mentioned darkening of the edge region of the intermediate image in the tube or a vignetting of the intermediate image in the tube, it is also possible to provide a glass block ahead of the lens element having positive refractive power. In that this glass block is configured as a beam splitter, an interface is made possible for a data in-coupling or data out-coupling in the imaging beam path in the tube.

Especially high ergonomic requirements can be satisfied in that the base part has a rotational joint having a rotational axis parallel to the optical axis of the imaging beam path.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
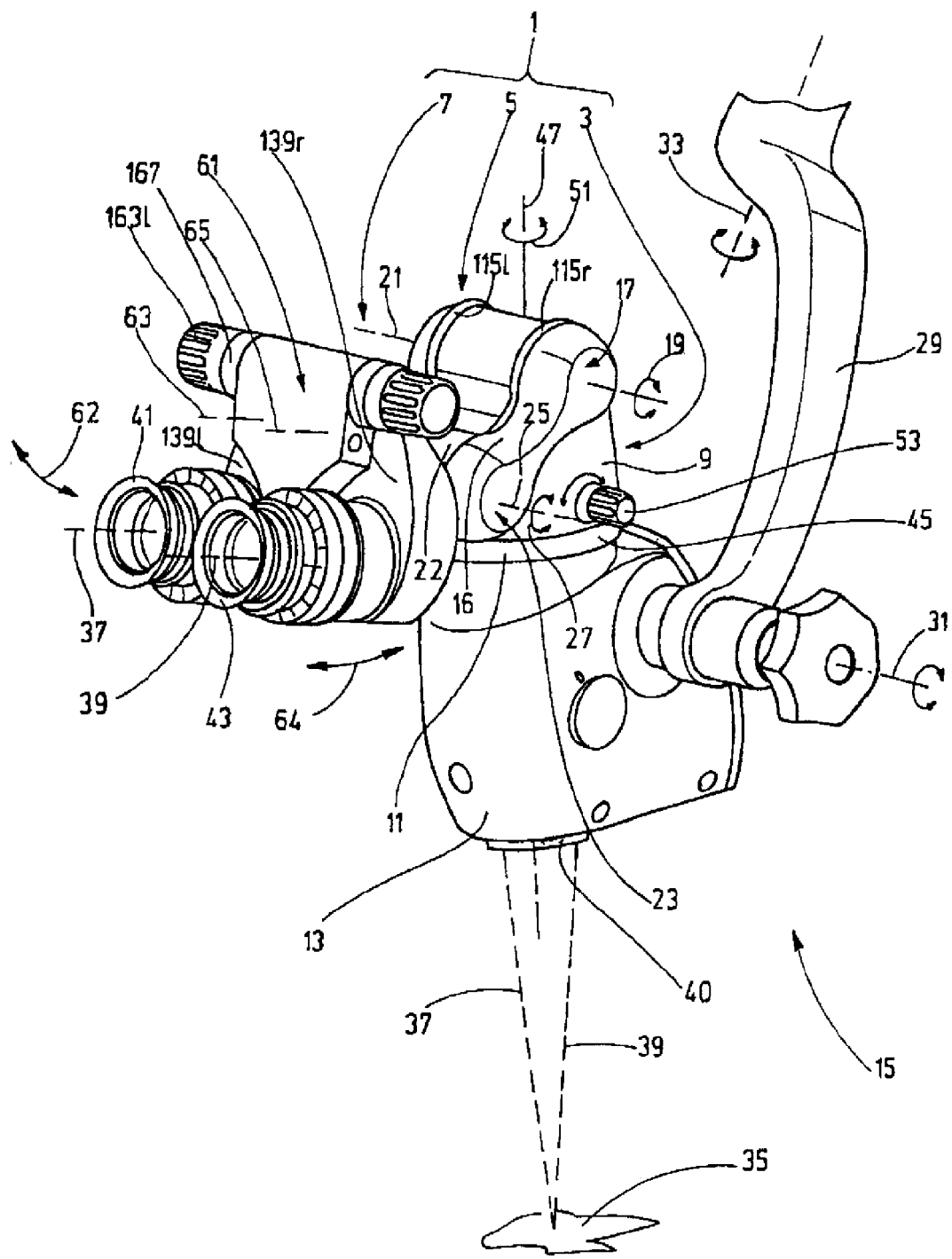
FIG. 1 is a perspective view showing a tube having an integrated magnification changer on the base body of a surgical microscope.

The tube 1 in FIG. 1 has a base part 3, an intermediate part 5, as well as an ocular part 7. The base part 3 includes a base housing 9. The base housing 9 is connected with a connecting piece 11 to the base body 13 of the surgical microscope 15. The intermediate part 5 has an intermediate part housing 16. The intermediate part 5 is pivotally movably mounted on the base part 3 via a rotational joint 17. The intermediate part 5 can thereby be moved about the rotational axis 21 in correspondence to the double arrow 19. The ocular part 7 includes an ocular part housing 22. The ocular part 7 is accommodated via a rotational joint 23 on the intermediate part 5. The rotational joint 23 has a rotational axis 25. The ocular part 7 can be pivoted on the rotational axis 25 and corresponds to the double arrow 27.

The base body 13 of the surgical microscope 15 is attached to the arm 29 of a surgical microscope stand (not shown). The surgical microscope 15 can be shifted with the tube 1 about the pivot axis 33 and the tilt axis 31 on the surgical microscope stand.

The surgical microscope 15 permits a viewing person to view an object region 35 via left and right stereoscopic imaging beam paths having optical axes (37, 39) through the left and right oculars (41, 43) with magnification. The left and right stereoscopic imaging beam paths pass through a common microscope main objective 40.

The base part 3 includes a rotational joint 45. In the rotational joint 45, the tube 1 can be moved relative to the base body 13 of the surgical microscope 15 about a rotational axis 47 in correspondence to the double arrow 51. The rotational axis 47 is parallel to the optical axes (37, 39) of the imaging beam path entering into the tube.

An adjustable afocal magnification system is disposed in the base body 13 of the surgical microscope 15. In the base part 3 of the tube 1, a further afocal magnification system is disposed for the left and right imaging beam paths. This magnification system is accommodated in a magnification changer which can be actuated by means of a rotary knob 53. The magnification changer in the tube permits a multifaceted adjustment of the magnification of the viewing images in the surgical microscope 15.

The left and right oculars (41, 43) are arranged in ocular receptacles (139l, 139r), respectively. The ocular receptacles (139l, 139r) can be pivoted about the axes (63, 65) for a pupil distance adjusting device 61 in correspondence to the double arrows (62, 64).

The tube 1 contains a tube lens system for each of the left and right imaging beam paths. The tube lens system is configured as a telesystem.

Figure 2:
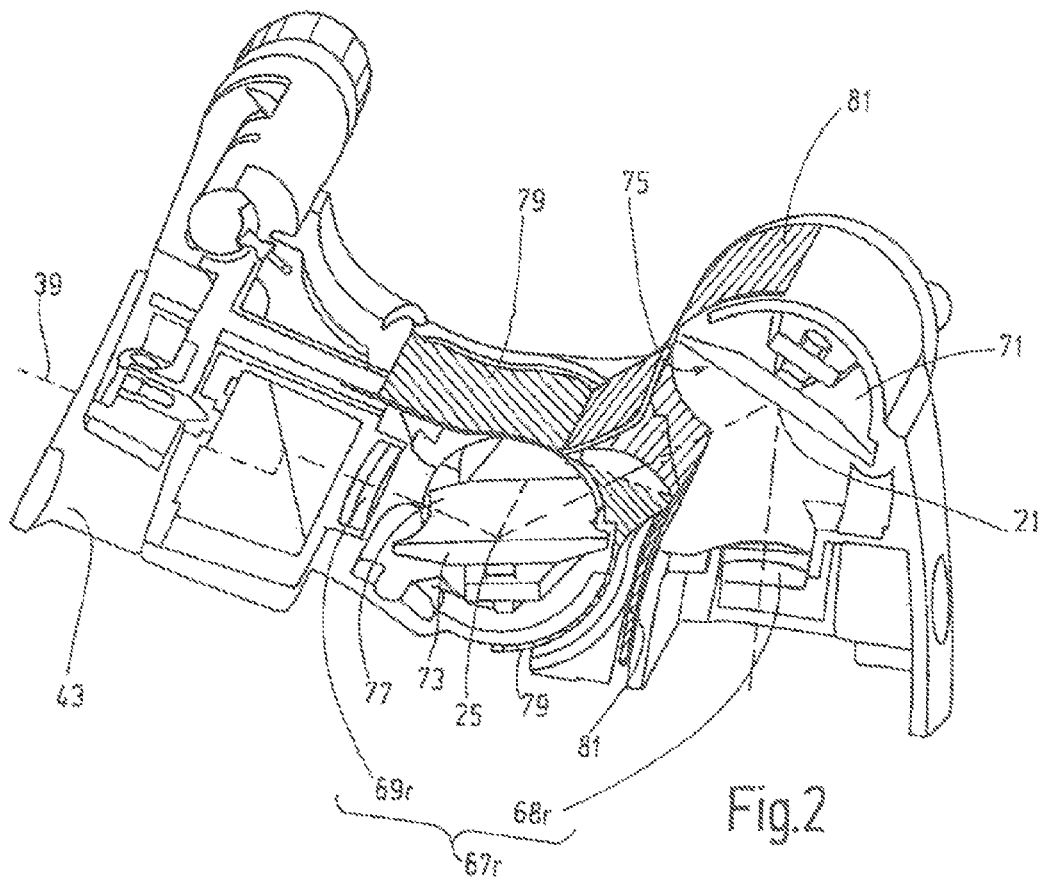
FIG. 2 is a three-dimensional section of an assembly of the tube.

FIG. 2 shows component assemblies of the tube 1 in a three-dimensional section with the right imaging beam path having the optical axis 39. The right imaging beam path passes through the right tube lens system 67r which has a lens unit 68r of positive refractive power and a lens unit 69r of negative refractive power.

For the left imaging beam path having the optical axis 37, the tube lens system 67 in tube 1 contains a left tube lens system, which has a lens unit having positive refractive power and a lens unit having negative refractive power.

Between the lens units (68r, 69r) of the tube lens system 67r, a first mirror element 71 and a second mirror element 73 are arranged in the imaging beam path having the optical axis 39. The same applies for the tube lens system in the imaging beam path having the optical axis 37. The mirror elements (71, 73) are pivotally-movably supported in the rotational axes (21, 25) of the tube 1. The rotational axes (21, 25) run in the mirror surfaces (75, 77) of the mirror elements (71, 73). The rotational axes (21, 25) intercept the optical axes (37, 39) of the left and right stereoscopic imaging beam paths perpendicularly. The first mirror element 71 directs the imaging beam paths 37 and 39 with the optical axes through the intermediate part 5 directly to the second mirror element 73. The imaging beam path is guided to the mirror element via the base part 3 of the tube 1. The imaging beam path is directed into the ocular part 7 via the second mirror element 73.

The tube 1 contains a first and a second housing covering (79, 81). The imaging beam paths having the optical axes (37, 39) pass through the tube 1 and are covered by means of the base housing 9, the intermediate part housing 16, the ocular part housing 22, and the two housing coverings (79, 81). The two housing coverings (79, 81) of the tube 1 are designed as components which are exactly identical in construction.

Figure 3:
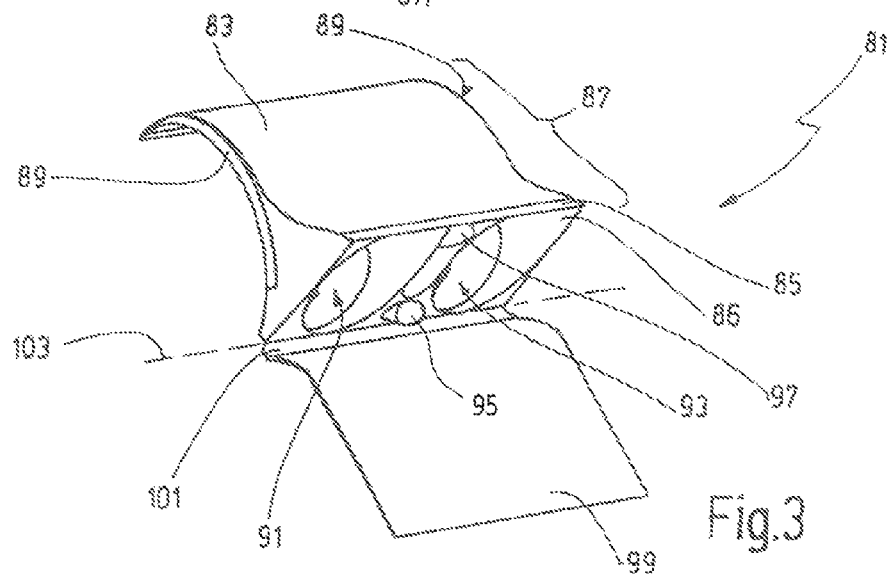
FIG. 3 shows a housing covering for covering the imaging beam path in the tube.

FIG. 3 shows the housing covering 81. The covering unit 81 includes a rigid cover section 83 having a support 85. The support 85 has a base surface 86. The rigid covering section 83 has an S-shaped outer contour 87. Two arcuate-shaped rails 89 are configured on the rigid cover section 83. The support 85 has two pass-through openings (91, 93) for the stereoscopic imaging beam paths having the optical axes (37, 39). A lug 95 is disposed on the support 85. The support 85 has a recess 97 which functions to accommodate the lug of the cover unit 79. The housing covering 81 has a flexible covering section 99. The flexible covering section 99 is connected via a film joint 101 to the rigid covering section 83. In the film joint 101, the flexible cover section 99 can be moved relative to the rigid cover section 83 about the rotational axis 103.

The two housing coverings (79, 81) are fixed to the intermediate part 5 of the tube 1. The two housing coverings (79, 81) are joined together on the base surfaces of the respective supports of the housing coverings (79, 81). The lug of the one housing covering projects into the recess for accommodating the lug of the other housing covering.

FIGS. 4 to 8 show the tube 1 in section having different pivot positions.

The base part 3 has a connecting piece 105 which is configured as a male dovetail coupling piece. The connecting piece 105 is connected to the base housing 9 via the rotational joint 45. In the base housing 9, an afocal magnification system (109l, 109r) is provided for each of the left and right imaging beam paths having optical axes (37, 39). The afocal magnification system is mounted in a stereoscopic galilei changer 107.

When the tube 1 is connected to the base body 13 of a surgical microscope 15, the imaging beam path having the optical axis 37 passes through the opening 108l in the connecting piece 105 of the tube 1 for a parallel beam path. An entry window 110l is disposed in the opening 108l. A corresponding opening 108r having a window 110r is formed in the connecting piece 105 for the imaging beam path having the optical axis 39.

The lens unit (68l, 68r) of positive refractive power of the tube lens system 67 is disposed between the afocal magnification system (109l, 109r) and the first mirror element 71.

The optical path length $L_{106,68}$ between the lens unit (68l, 68r) having positive refractive power and the opening (108l, 108r) is longer than the optical path length $L_{68,21}$ between the lens unit (68l, 68r) having positive refractive power and the mirror element 71. This applies in a corresponding manner for the imaging beam oath having the optical axis 39.

The mirror element 71 is movable about the rotational axis 21 of the rotational joint 17 and is coupled by a reduction gear to the rotational joint 17. For a movement of the rotational joint by the angle φ, the reduction gear causes the mirror element 71 to move by the angle φ/2 in a direction corresponding to the movement of the intermediate part 5. This ensures that the mirror element 71 directs the imaging beam path having optical axes (37, 39) into the pass-through openings (91,93), respectively, of the housing coverings (79, 81) onto the second mirror element 73 for each position of the rotational joint 17.

The mirror element 73 is also coupled to the rotational joint 23 via a reduction gear in correspondence to the mirror element 71. In a movement of the ocular part 7 about the rotational axis 25 of the rotation joint 23 on the intermediate part 5 by the angle φ, the mirror 73 is moved by the angle φ/2 in an angular position corresponding to the movement of the ocular part 7.

The imaging beam path is supplied to the mirror element 73 from mirror element 71 and this mirror element 73 directs the imaging beam path having the optical axes (37, 39) into the ocular part 7 of the tube 1 in such a manner that the optical axes (37, 39) align respectively with the optical axes of the corresponding lens units having negative refractive power (69l, 69r). In this way, the imaging beam path runs with the optical axes (37, 39) from the openings of the base part 3 of the tube 1 with the same stereo basis to the lens units (69l, 69r) having negative refractive power.

The housing coverings (79, 81) are fixed in the intermediate part 5. The rails 89 on the rigid cover section 83 each engage in a slot of a cover element (115l, 115r) laterally covering the intermediate part 5. The flexible covering section 99 of the cover unit 81 projects into a slit 116 which is configured on the base housing 9.

Figure 4:
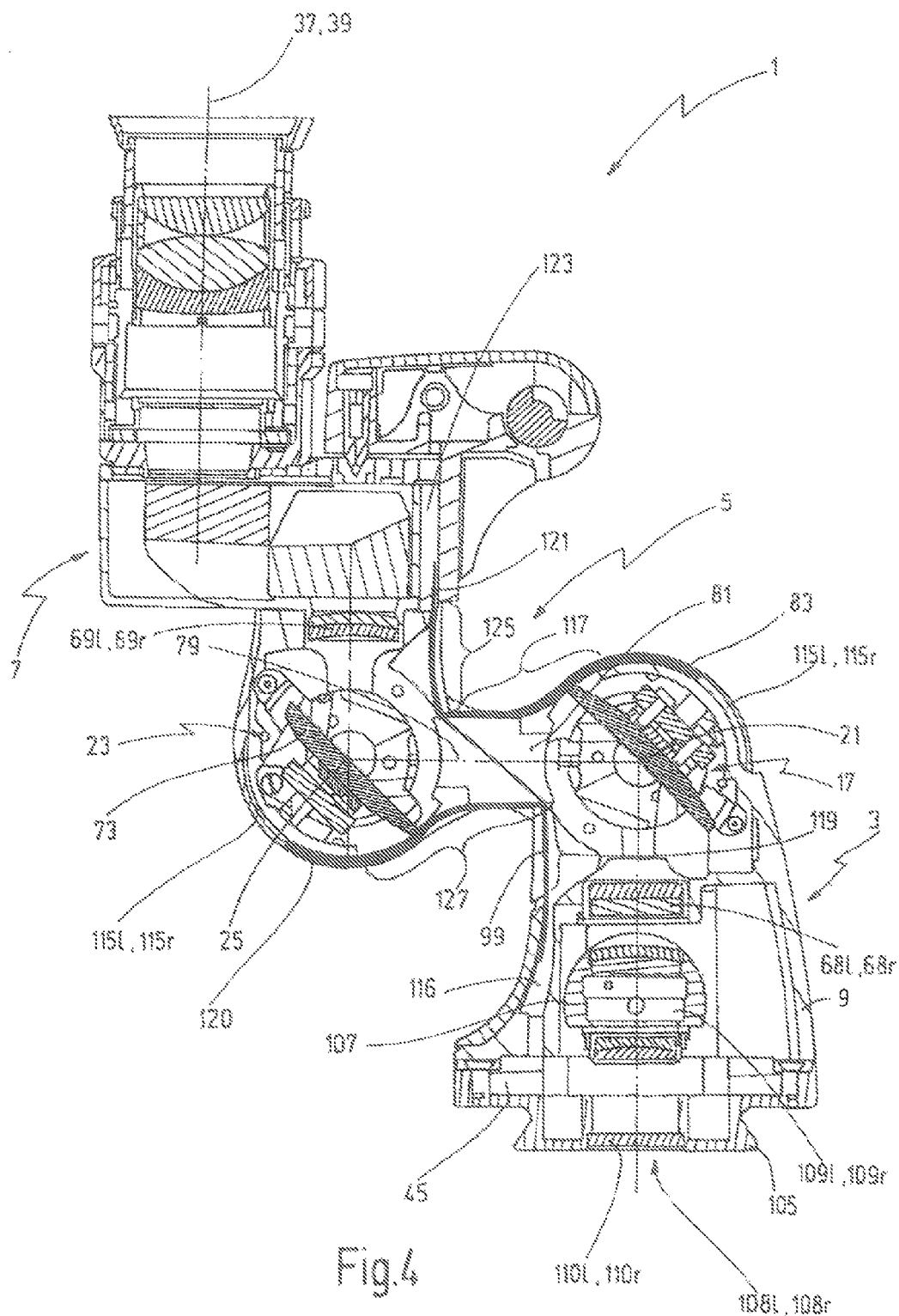
FIGS. 4 to 8 show sections of the tube in different pivot positions.

The imaging beam path is covered in the region 117 for a position of the tube 1 shown in FIG. 4 by means of the rigid covering section 83. The flexible cover section 99 then covers the imaging beam path in the tube 1 in the region 119.

The rigid cover section 120 of the cover unit 79 is held to the cover elements (115l, 116r) covering the intermediate part 5 laterally. The flexible cover section 121 of the cover unit 79 projects into a slit 123 which is configured in the ocular part 7. The flexible cover section 121 covers an imaging beam path in the tube 1 in the region 125. The imaging beam path, which passes through the tube 1, is covered in the region 127 by the rigid cover section 120.

The intermediate part 5 can be moved on the base part 3 of the tube 1 between a folded position and an unfolded position. The same applies for the movement of the ocular part 7 on the intermediate part 5.

Figure 5:
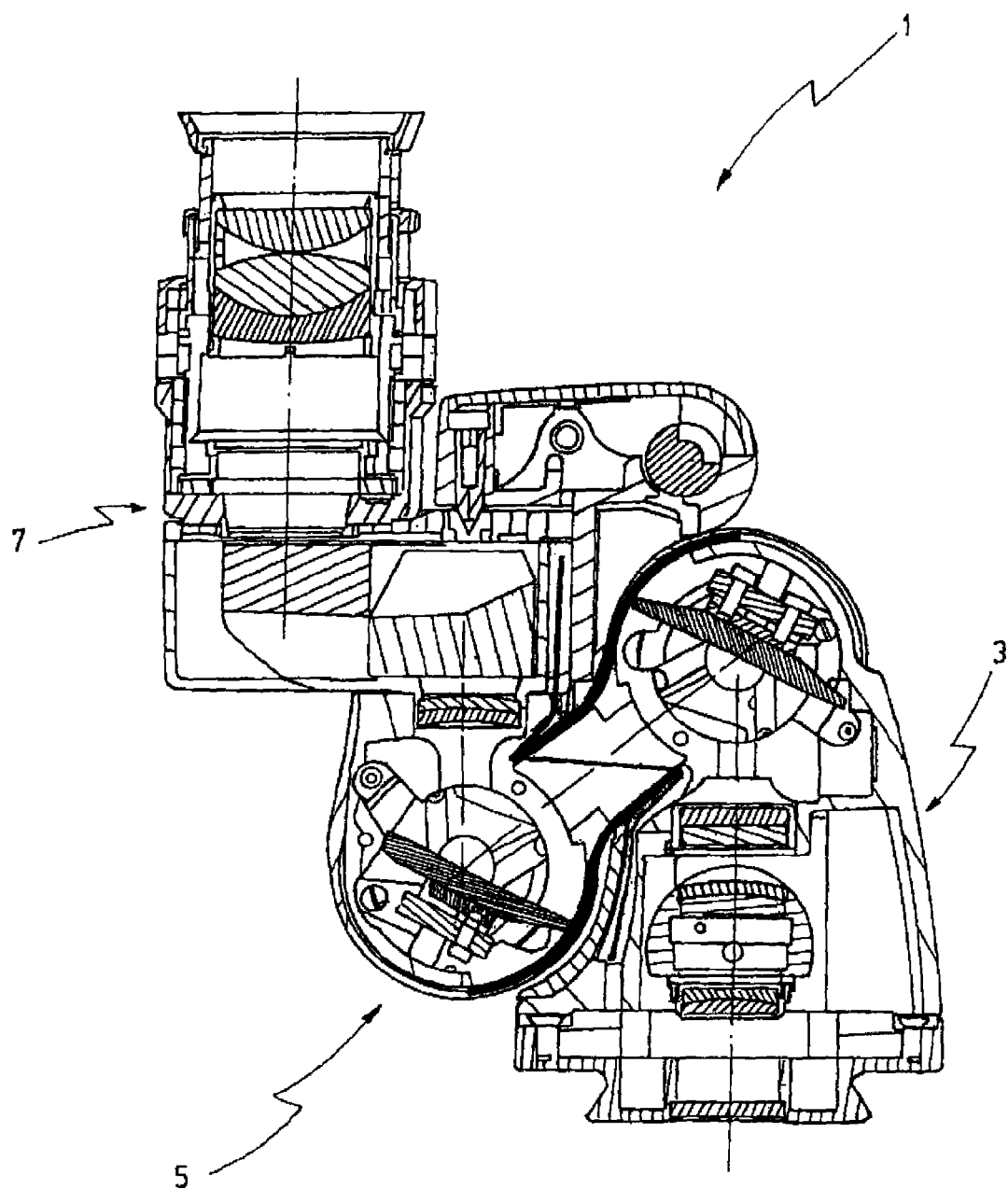

FIG. 5 shows the tube 1 in a setting wherein the intermediate part 5 as well as the ocular part 7 are disposed in a folded position. In the housing section 149, the outer contour of the base housing 9 is configured with a concave-convex outer contour accommodating the convex-concave geometry of the intermediate part housing 16 in section 151. In the section 155, the outer contour of the ocular part 7 is adapted to the convex-concave geometry of the intermediate part 5 in the section 159.

Figure 6:
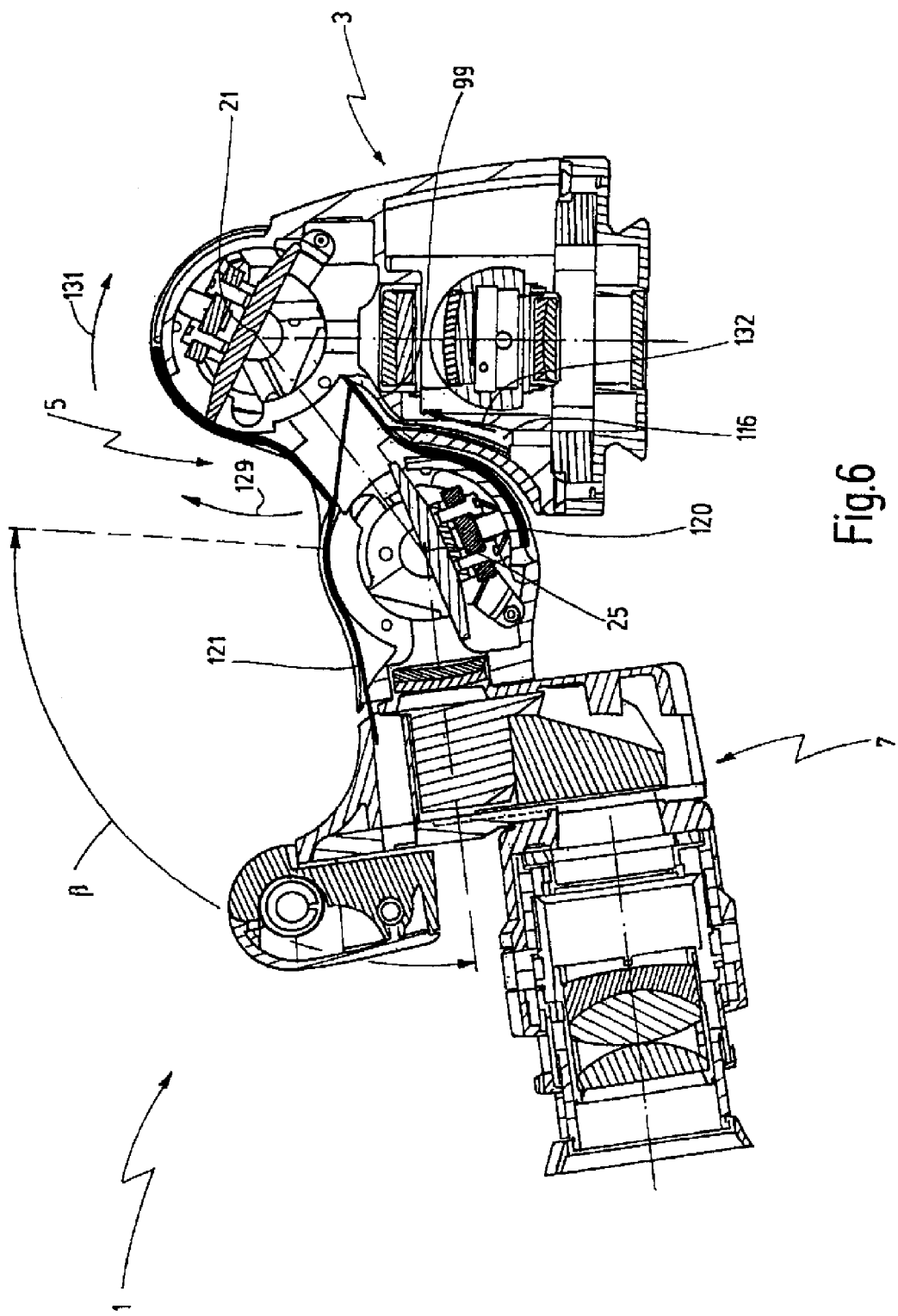
Figure 7:
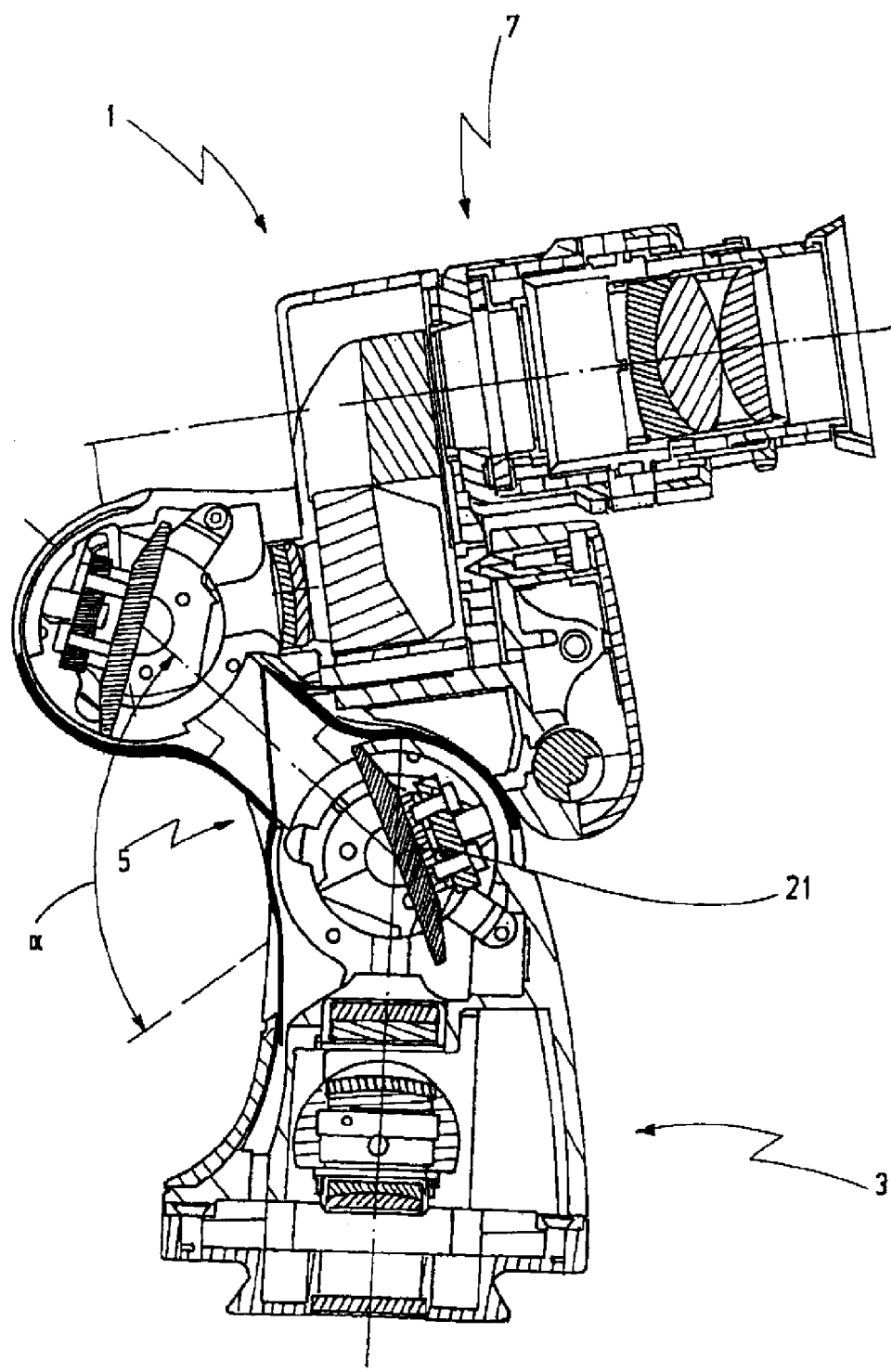

FIG. 6 shows the tube 1 when the intermediate part is positioned in the folded position and the ocular part 9 is in the unfolded position. In the setting of FIG. 7, the intermediate part 5 of the tube is disposed in the unfolded position and the ocular part 7 is in the folded position.

The rotational joint 17 of the tube 1 can be displaced over an angular range α=80° about the rotational axis 21. The rotational joint 23 is movable about the rotational axis 25 over an angular range β=100°.

When the intermediate part 5 on the base part 3 is moved about the rotational axis 21 in correspondence to the arrow 129, the rigid cover section 83 is rotated about the rotational axis 21 in correspondence to the arrow 131. With this, the flexible cover section 99 moves in the manner of a coulisse or jalousie in the direction of the arrow 132 out of the slit 116 on the base housing 9. The same applies to the movement of the rigid cover section 120 and the flexible cover section 121 for a movement of the ocular part 7 about the rotational axis 25 of the rotational joint 23.

Figure 8:
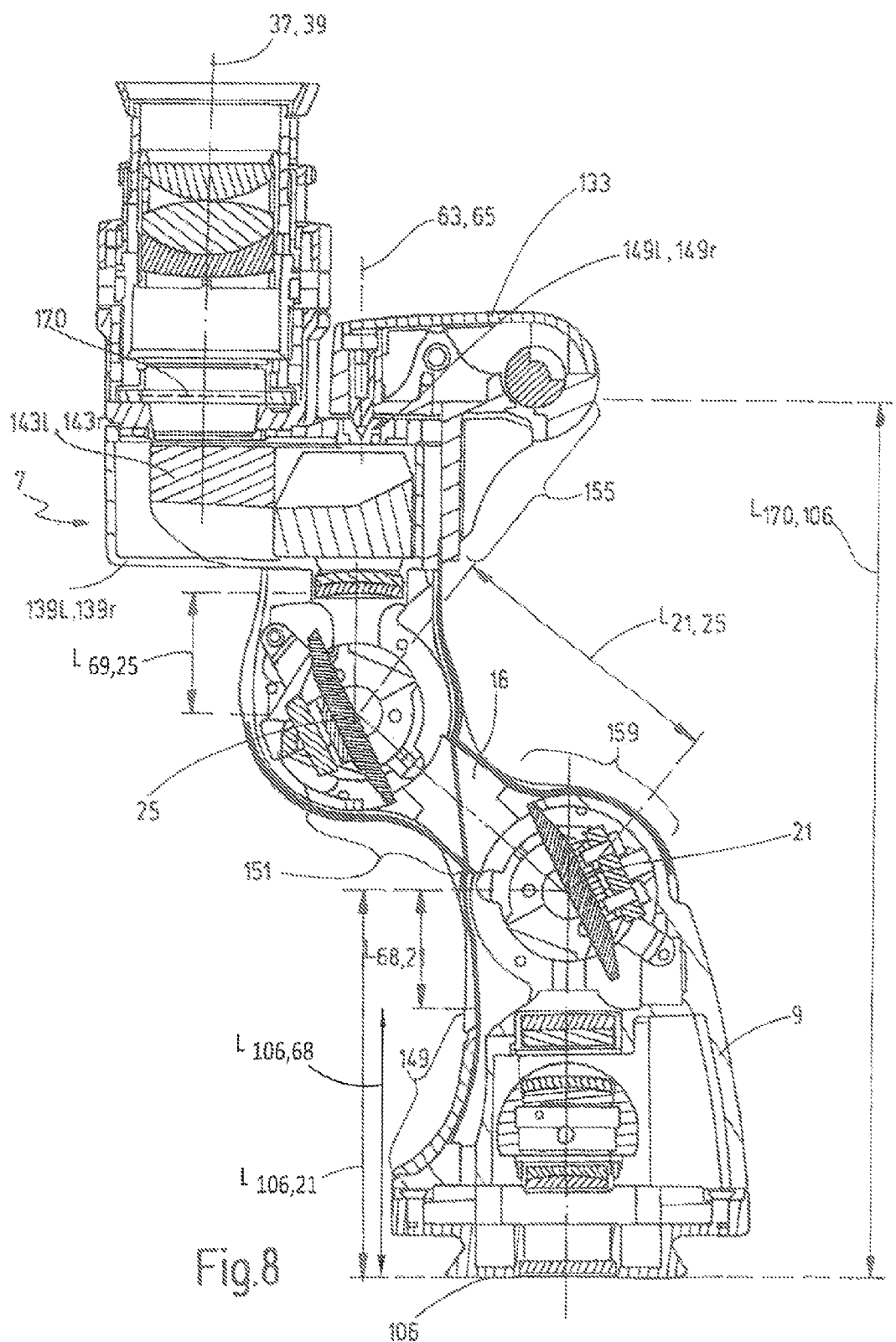

FIG. 8 shows the tube 1 in an unfolded position of intermediate part 5 and ocular part 7.

For the distance $L_{21,25}$ of the rotational axis 21 and the rotational axis 25, the following applies: $L_{21,25}$=53 mm. The distance $L_{106,21}$ of the rotational axis 21 from the end surface 106 of the connecting piece is $L_{106,21}$=72 mm. The distance $L_{68,21}$ of the lens unit (68l, 68r) having positive refractive power from the rotational axis 21 is $L_{68,21}$=23 mm. For the distance of the lens unit (69l, 69r) having negative refractive power from the rotational axis 25, the following applies: $L_{69,25}$=23 mm. The optical path length between the lens unit (68l, 68r) having positive refractive power and the lens unit (69l, 69r) having negative refractive power is 99 mm. The focal length f1 of the lens unit (68l, 68r) having positive refractive power is f1=157 mm. For the focal length f2 of the lens unit having negative refractive power (69l, 69r), the following applies: f2=236 mm. The distance $L_{170,106}$ of the plane 170 for the intermediate image in the unfolded position of the tube 1 from end face 106 of the connecting piece is then $L_{170,106}$=174 mm.

The ocular part 7 of the tube 1 has a section (139l, 139r) wherein respective lens units having negative refractive power (69l, 69r) are arranged for the left and right imaging beam paths with the optical axes (37, 39).

For the accommodation of the oculars (41, 43), the tube has, at the section 133, pivotally movably mounted sections (139l, 139r), respectively, wherein respective Porro systems (143l, 143r) are provided for image reversal.

For the pupil distance adjustment, the sections (139l, 139r) having respective Porro systems (143l, 143r) and respective oculars (41, 43) can be shifted about the rotational axes (63, 65) of the rotational joints (149l, 149r) which are aligned with the optical axes (37, 39) of the lens units (69l, 69r) having negative refractive power.

Figure 9:
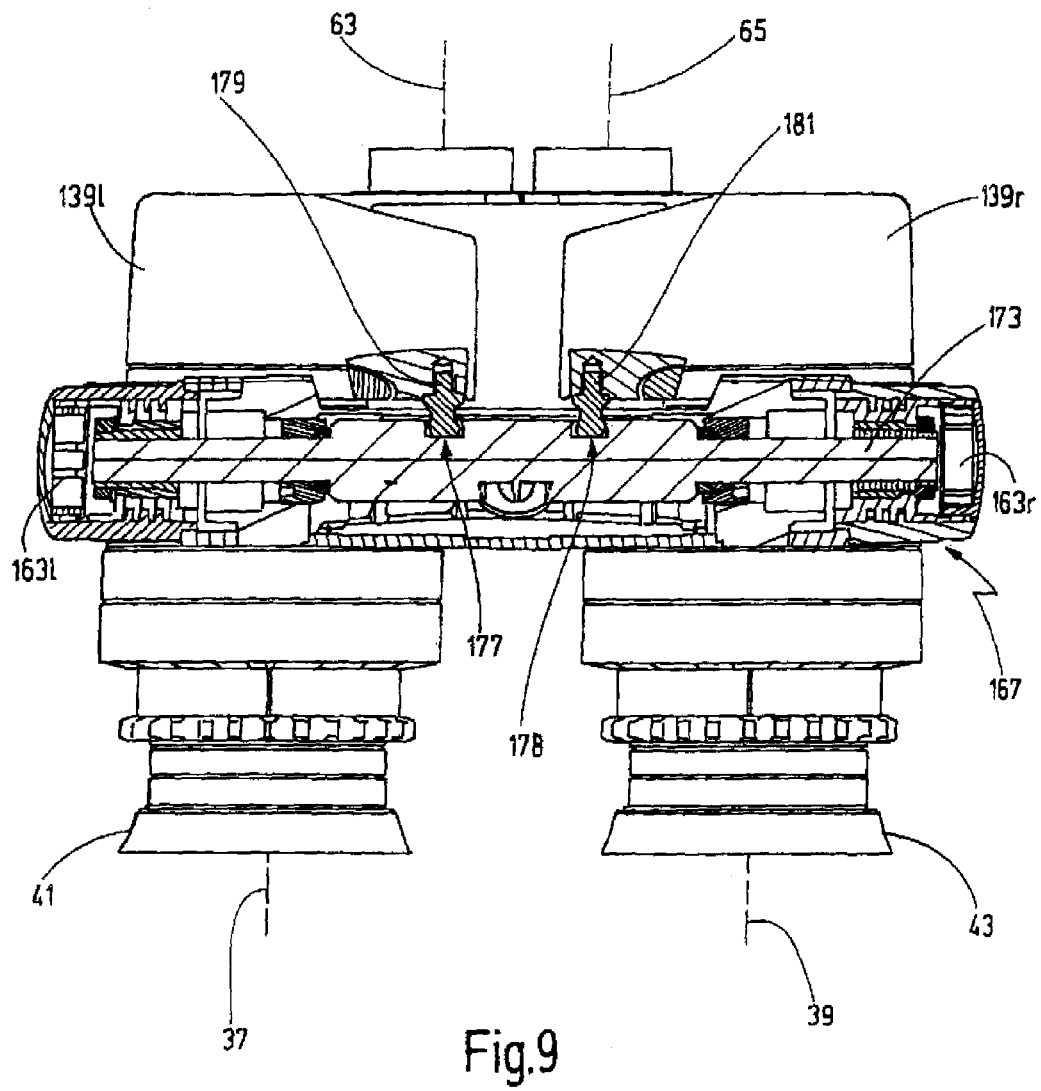
FIG. 9 shows the ocular in-view of the tube with a device for adjusting the pupil distance.

FIG. 9 shows the ocular in-view of the tube 1 having left and right oculars (41, 43) and pivotally movable sections (139l, 139r) which can be pivoted by means of a drive 167 about the axes (63, 65). The drive 167 has rotational knobs (163l, 163r). The drive 167 includes a shaft 173 wherein a first slot curve 178 and a second slot curve 177 are formed. The slot curves (177, 178) each operate on a slot stone (179, 181). The slot stone 179 is fixed in the pivotally movable section 139. The slot stone 181 is fixed in the pivotally movable section (139l, 139r). By rotating the shaft 173 and by means of the slot curves (177, 178), a pivot position of the sections (139, 139r) is effected which changes the pupil distance of the oculars (41, 43). The oculars (41, 43) are accommodated in the sections (139l, 139r).

Figure 10:
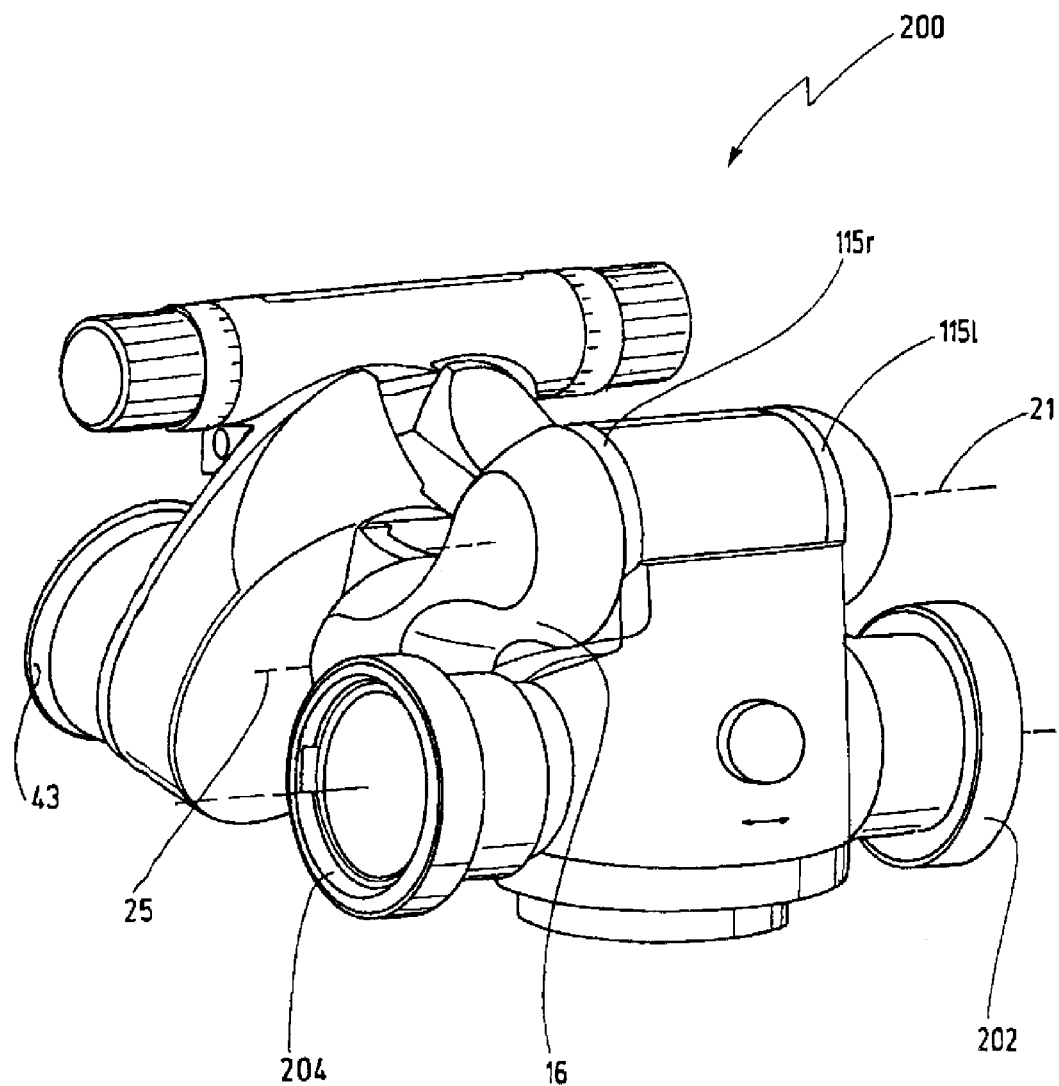
FIG. 10 shows a tube having an integrated beam splitter and interfaces for connecting to documentation units; and, FIG. 11 shows the imaging beam path of the tube with integrated beam splitter.

FIG. 10 shows a modified tube 200 for a surgical microscope having two interfaces (202, 204) for the connection of documentation units, for example, documentation units in the form of a camera.

Figure 11:
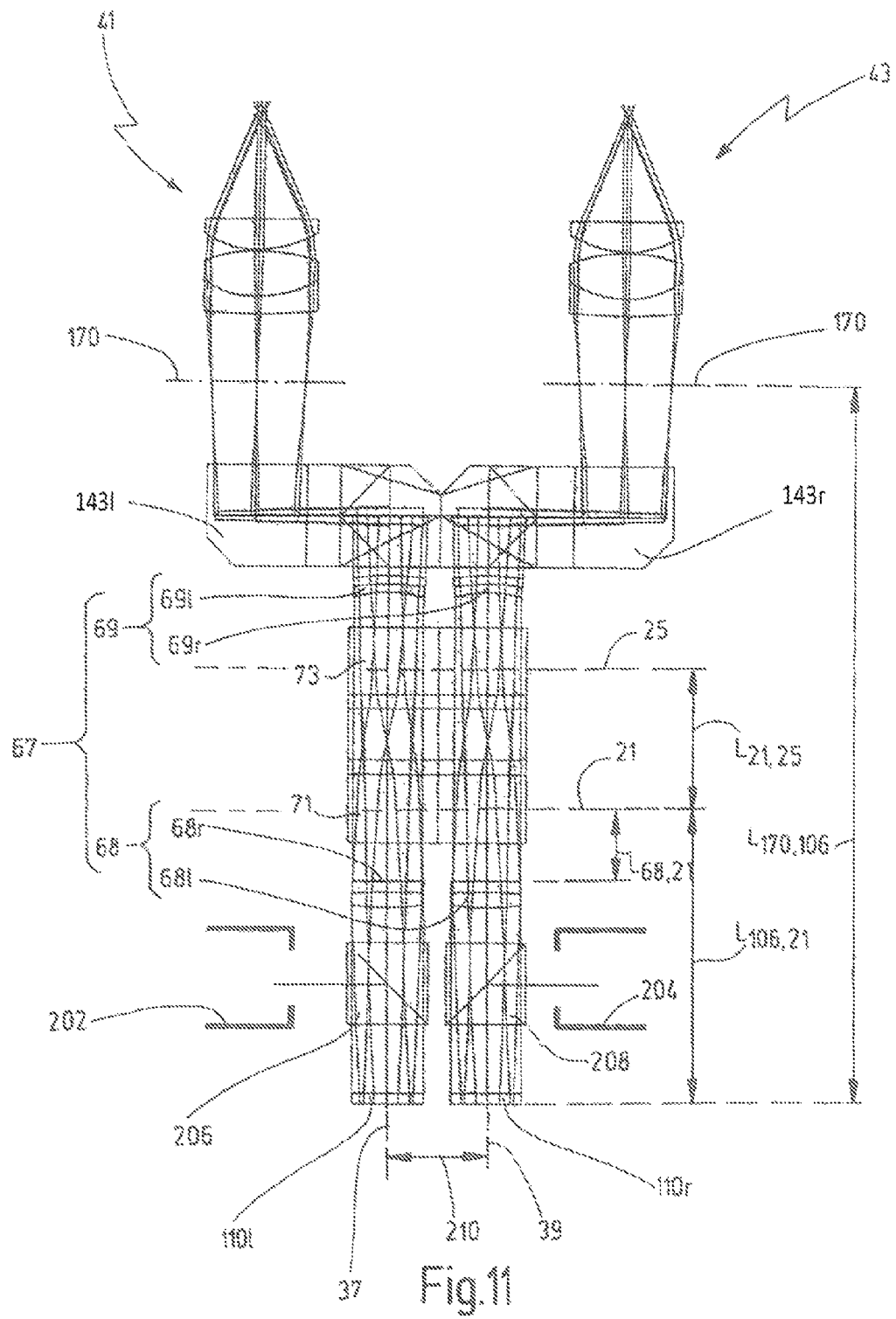

FIG. 11 shows the optical component groups of the tube 200. These have the same reference characters insofar as the component groups of tube 200 correspond to the component groups of the tube 1 having a magnification changer which is explained with reference to FIGS. 1 to 9.

In lieu of a magnification changer in the left and right imaging beam paths, the imaging beam path having the optical axes (37, 39) pass through a beam splitter 206 and through a beam splitter 208 in the tube 200. The beam splitter 206 is mounted in the left imaging beam path having the optical axis 37. The beam splitter 208 is correspondingly in the right imaging beam path having the optical axis 39 between the lens unit 68*l* having positive refractive power and the window in the opening 108*l* on the connecting piece of the tube 200. A fraction of the left imaging beam path is directed to the interface 202 by the beam splitter 206. The beam splitter 208 couples out a portion of the right imaging beam to the interface 204.

The left and right imaging beam paths pass through the windows (110*l*, 110*r*) in the opening on the connecting piece and pass through the lens units of positive refractive power (68*l*, 68*r*) of the left and right tube lens systems (67*l*, 67*r*). The imaging beam path is then directed by the first and second mirror elements (71, 73) in the intermediate part 5 of the tube 200 to the lens units (69*l*, 69*r*) having negative refractive power. The lens units (69*l*, 69*r*) are mounted in the ocular part 7 of the tube. The tube lens system 67 is configured as a telesystem and generates an intermediate image in the intermediate image plane 170. The intermediate image can be viewed by the viewing person with an eye adapted to infinity through the oculars (41, 43) with magnification. The imaging beam path having the optical axes (37, 39) is guided from the connecting piece of the tube 200 having windows (110*l*, 110*r*) via the first and second mirror elements (71, 73) to the lens units (69*l*, 69*r*) having negative refractive power with a constant stereo basis 210.

It is noted that the invention relates to a tube 1 for a surgical microscope. The tube 1 has a base part 3, an intermediate part which is pivotable about a rotational axis on the base part 3, and an ocular part 7 which is pivotable about a rotational axis 25 on the intermediate part 5. The imaging beam path is guided through the base part 3, the intermediate part 5 and the pivotable ocular part 7. The tube 1 has a tube lens system 67 which passes a parallel imaging beam path (37, 39) into an intermediate image. The imaging beam path (37, 39) enters via an opening 108 into a connecting piece 105 of the base part 3. The tube has a first adjustable mirror element 71 which can be moved on the base part 3 about the rotational axis 21. The tube includes a further adjustable mirror element 73 which is movable on the intermediate part 5 about the rotational axis 25. The first mirror element 71 directs the imaging beam path (37, 39), which enters via the connecting piece 105, to the further mirror element 73. According to the invention, the tube lens system is a telesystem 67, which has a lens unit having positive refractive power (68*l*, 68*r*) and a lens unit having negative refractive power (69*l*, 69*r*). The first mirror element 71 and the further mirror element 73 are arranged in the imaging beam path (37, 39) between the lens unit having positive refractive power (68*l*, 68*r*) and the lens unit having negative power (69*l*, 69*r*).

It is understood that the foregoing description is that of the preferred embodiments of the invention and that various changes and modifications may be made thereto without departing from the spirit and scope of the invention as defined in the appended claims.

What is claimed is:

1. A tube for a surgical microscope comprising:
    a base part;
    an intermediate part pivotable on said base part about a first rotational axis;
    an ocular part pivotable on said intermediate part about a second rotational axis;
    said base part, said intermediate part and said ocular part conjointly defining a left imaging beam path and a right imaging beam path passing therethrough;
    said base part having a connecting piece defining an opening through which said imaging beam paths enter, wherein said imaging beam paths are parallel at said opening;
    a tube lens system for transferring said imaging beam paths entering in parallel through said opening in said connecting piece into an intermediate image plane;
    a first displaceable mirror movable about said first rotational axis;
    a second displaceable mirror movable about said second rotational axis;
    said first displaceable mirror directing said imaging beam paths entering via said connecting piece to said second displaceable mirror;
    said tube lens system being a telesystem including a first lens unit having positive refractive power and a second lens unit having negative refractive power; and,
    said first displaceable mirror and said second displaceable mirror being disposed in said imaging beam paths between said first lens unit and said second lens unit.

2. The tube of claim 1 wherein said first lens unit and said first displaceable mirror conjointly define a first optical path length therebetween; said opening in said connecting piece and said first lens unit define a second optical path length; and, said first optical length is shorter than said coed optical path length.

3. The tube of claim 1, wherein said left and right imaging beam paths are conducted at constant stereo basis from said opening in said connecting piece to said second displaceable mirror.

4. The tube of claim 1, wherein said second lens unit is mounted in said ocular part.

5. The tube of claim 1, wherein said ocular part has a first section hinged to said intermediate part and a second section accommodated on a rotational joint pivotable about an optical axis of said imaging beam paths passing through said ocular part; and, said second section has a receptacle for an ocular.

6. The tube of claim 5, further comprising a porro system for image reversal being mounted in said second section.

7. The tube of claim 5, further comprising a drive for pivoting said second section.

8. The tube of claim 6, wherein said second lens unit is disposed between said second displaceable mirror and said porro system for image reversal.

9. The tube of claim 1, further comprising an afocal magnification system disposed between said first lens unit and said opening in said connecting piece.

10. The tube of claim 9, wherein said afocal magnification system is adjustable via a galilei changer.

11. The tube of claim 1, further comprising a glass block disposed between said first lens unit and said opening in said connecting piece.

12. The tube of claim 1, further comprising a beam. splitter disposed between said first lens unit and said opening in said connecting piece.

13. The tube of claim 1, wherein said base part has a rotational joint defining a rotational axis parallel to an optical axis of said imaging beam paths passing through said base part.

* * * * *

UNITED STATES PATENT AND TRADEMARK OFFICE
CERTIFICATE OF CORRECTION

PATENT NO. : 8,514,488 B2
APPLICATION NO. : 12/805663
DATED : August 20, 2013
INVENTOR(S) : Christian Lücke et al.

It is certified that error appears in the above-identified patent and that said Letters Patent is hereby corrected as shown below:

In the Specification:

In Column 6:
Line 54: delete "(681," and substitute -- (68l, -- therefor.
Line 59: delete "oath" and substitute -- path -- therefor.

In the Claims:

In Column 10:
Line 26: add -- path -- before "length".
Line 26: delete "coed" and substitute -- second -- therefor.
Line 56: delete "beam." and substitute -- beam -- therefor.

Signed and Sealed this
Twenty-second Day of October, 2013

Teresa Stanek Rea
*Deputy Director of the United States Patent and Trademark Office*